US00PP30890P2

(12) United States Plant Patent
Cesarini

(10) Patent No.: US PP30,890 P2
(45) Date of Patent: Sep. 24, 2019

(54) ***BUXUS* PLANT NAMED 'BHGC01'**

(50) Latin Name: *Buxus sempervirens*
Varietal Denomination: BHGC01

(71) Applicant: Gabriel Cesarini, Denton, MD (US)

(72) Inventor: Gabriel Cesarini, Denton, MD (US)

(73) Assignee: Plant Development Services, Inc., Loxley, AL (US)

( * ) Notice: Subject to any disclaimer, the term of this patent is extended or adjusted under 35 U.S.C. 154(b) by 0 days.

(21) Appl. No.: 15/998,039

(22) Filed: Jun. 15, 2018

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226
CPC ..... A01H 6/00; A01H 5/00; A01H 5/02
See application file for complete search history.

*Primary Examiner* — Keith O. Robinson
(74) *Attorney, Agent, or Firm* — Cassandra Bright

(57) ABSTRACT

A new and distinct *Buxus* cultivar named 'BHGC01' is disclosed, characterized by a distinctive a globular growth habit and good performance in shade. Plants grow slowly, have dark green foliage. Foliage is distinctly elongated. The new cultivar is a *Buxus*, suitable for ornamental garden purposes.

2 Drawing Sheets

Figure 1:
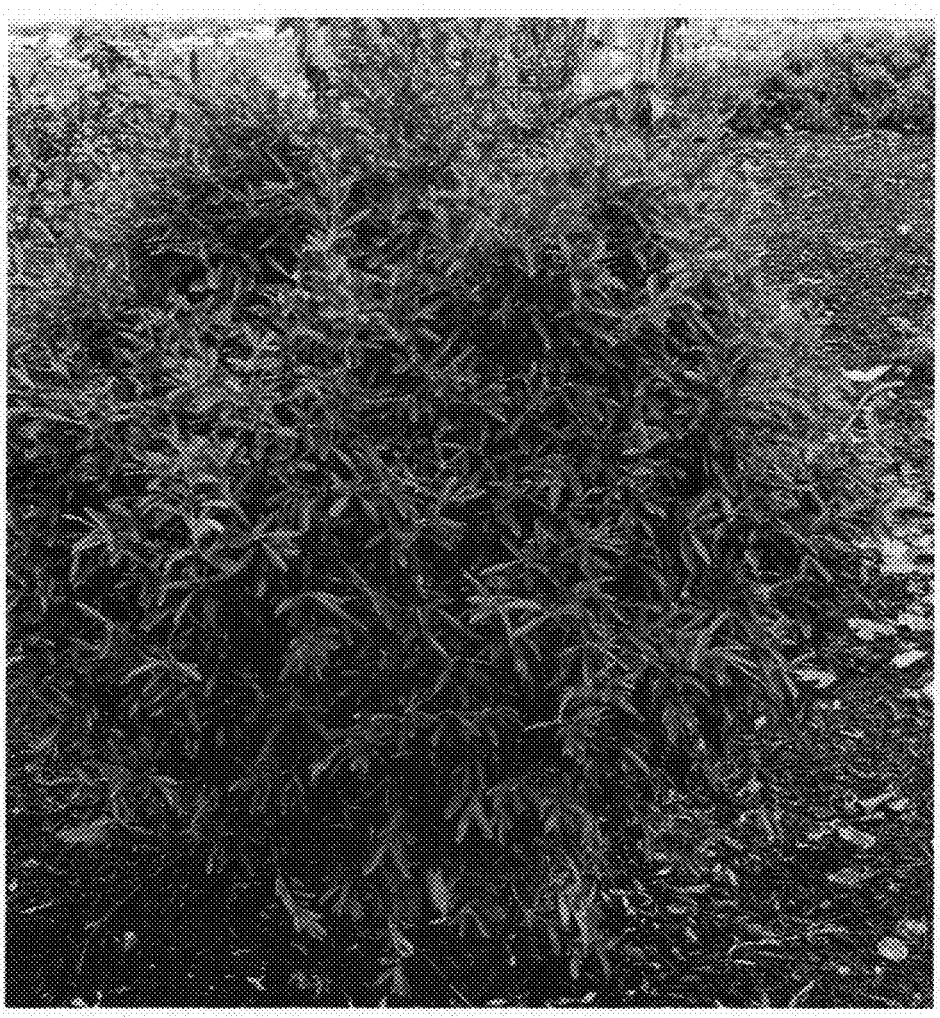

Latin name of the genus and species: *Buxus sempervirens*.
Variety denomination: 'BHGC01'.

BACKGROUND OF THE INVENTION

The new cultivar is a product of chance discovery by the inventor. This new variety, hereinafter referred to as 'BHGC01', was discovered as a naturally occurring, whole plant mutation by the inventor, Gabriel Cesarini. The interesting new mutation was discovered in a private garden in Ridgely, Md. among plants of unpatented *Buxus sempervirens* during an unrecorded date between approximately 1995 and 1997.

After identifying the new variety as a potentially interesting selection, the inventor first organized propagation of 'BHGC01' by vegetative cuttings at a commercial nursery in Warwick, Md. around 1997. The inventor transferred the cuttings to his personal garden. Over many years the inventor continued controlled observation of this interesting mutation. After many years the inventor observed that while the plant continued to exhibit a healthy overall appearance, the plant remained very small. Additionally, the inventor observed the new variety thrived in shade and maintained dark green foliage year round. After several years of observation, the inventor propagated further plant material to assess the stability of these interesting traits. At least three generations have been reproduced and have shown that the unique features of this cultivar are stable and reproduced true to type.

SUMMARY OF THE INVENTION

The cultivar 'BHGC01' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'BHGC01'. These characteristics in combination distinguish 'BHGC01' as a new and distinct *Buxus* cultivar:

1. Excellent performance in shade.
2. Dark green foliage.
3. Mature size of approximately two feet wide and three feet tall.
4. Elongated foliage.

COMPARISON TO PARENT VARIETY

'BHGC01' is similar in most horticultural characteristics to the parent variety. Plants of the new cultivar 'BHGC01' however have a slower growth habit and smaller mature size than the parent variety. Additionally, the parent variety does not exhibit the shade tolerance found with 'BHGC01'.

COMMERCIAL COMPARISON

'BHGC01' is similar in most horticultural characteristics to the unpatented commercial variety *Buxus sempervirens* 'Vardar Valley'. Plants of the new cultivar 'BHGC01' however differ in the following;

1. The new variety has darker green foliage.
2. The new variety has elongated foliage, 'Vardar Valley' has orbicular foliage.
3. Plants of the new variety have a smaller mature width than plants of 'Vardar Valley'.

'BHGC01' is similar in most horticultural characteristics to the patented commercial variety *Buxus semperviren* 'MonAlex', U.S. Plant Pat. No. 27,647. Plants of the new cultivar 'BHGC01' however differ in the following;

1. The new variety has darker green foliage.
2. The new variety has elongated foliage, 'MonAlex' has small, orbicular foliage.
3. Plants of the new variety have a globular overall shape, plants of 'MonAlex' are distinctively conical in shape.

BRIEF DESCRIPTION OF THE PHOTOGRAPHS

The accompanying photograph in FIG. 1 illustrates in full color a typical plant of 'BHGC01' grown outdoors in Maryland. The plant is approximately 20 years old, and is grown in a shady garden position.

Figure 2:
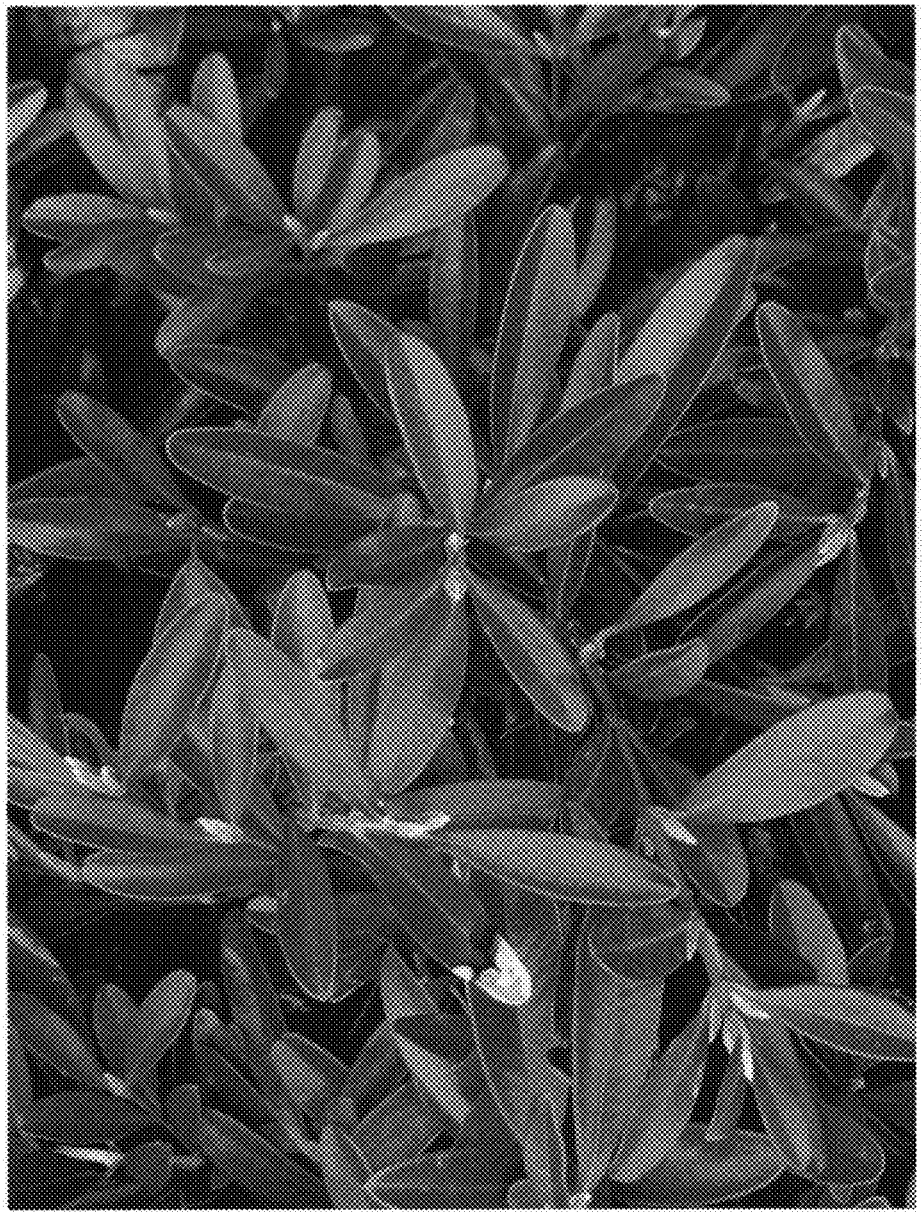

FIG. 2 illustrates a close-up view of the foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BHGC01' plants grown outdoors in Loxley, Ala. Plants are approximately 2 years old, in a 3 gallon nursery container. Measurements and numerical values represent averages of typical plant types.

Botanical classification: *Buxus sempervirens* 'BHGC01'.

PROPAGATION

Time to rooting: About 10 to 14 days at 25° C. to 30° C.

Time to produce a rooted young plant: About 45 to 60 days at 25° C. to 30° C.

Root description: Fibrous, very well branched. Colored near RHS Brown 199B, 199C.

PLANT

Growth habit: Evergreen woody shrub with a globular shape.

Height: Approximately 30 cm. after 2 years.

Plant spread: Approximately 30 cm at widest point.

Typical growth rate: Slow for species.

Branching characteristics: Very dense branches. No single central stem. Approximately 5 central upright branches, each of these with dense opposite branching occurring at an internode length on average 2.0 cm. Lateral stems are held at an angle of approximately 15 degree from the central branch.

Length of lateral branches: Average range 10 to 20 cm.

Diameter of lateral branches: Approximately 0.4 to 0.7 cm.

Lateral branch shape in cross section: Generally round.

Lateral branch strength: Very strong, not easily broken.

Lateral branch color:

*Young*.—Near Green 143C.

*Mature*.—Near RHS Greyed-Yellow 162C. Thin scales near Greyed-Orange 166A.

Lateral branch texture: Scaly and rough.

Internode length: Average range 1.2 to 2.0 cm.

Lenticels present: No.

FOLIAGE

Leaf:

*Arrangement*.—Opposite.

*Type*.—Simple.

*Shape of blade*.—Obovate.

*Average length*.—Average range 4.0 to 5.0 cm.

*Average width*.—Approximately 1.4 cm.

*Apex*.—Young foliage short mucronate. Mature foliage emarginate or round.

*Base*.—Tapered.

*Attachment*.—Petiolate. Reduced petiole.

*Margin*.—Entire.

*Texture of top surface*.—Glabrous.

*Texture of bottom surface*.—Glabrous.

*Appearance of top surface*.—Very glossy.

*Appearance of bottom surface*.—Matte.

*Leaf internode length*.—Average 1.0 cm.

*Color*.—Young foliage upper side: Near RHS Yellow-Green 144A. Young foliage under side: Near RHS Yellow-Green 144A. Mature foliage upper side: Near Green 139A. Mature foliage under side: Near RHS Yellow-Green 146B.

*Venation*.—Type: Pinnate. Venation color upper side: Near RHS Yellow-Green 144B. Venation color under side: Near RHS Yellow-Green 144D.

*Durability of foliage to stresses*.—Flexible and resistant to breakage.

*Fragrance*.—Musty foliage scent.

Petiole:

*Length*.—Average 2 to 3 mm.

*Diameter*.—1 mm.

*Pubescence*.—None, all surfaces glabrous.

*Color*.—Upper Surface near RHS Yellow-Green 144B. Lower Surface Near RHS Yellow-Green 144D.

FLOWER

Flowering inconsistent and infrequent. Flowering can occur in Spring, but, not consistently each year.

Inconspicuous apetalous flowers in axillary clusters may be produced. Clusters about 1 cm wide and 8 mm deep, with 4 to 7 flowers per cluster. Flowers colored near Orange-White 159D. Flowers about 2 mm wide and 2 mm tall.

Reproductive organs less than 1 mm, misshapen to the point of unidentifiable individual parts.

Fruits and seeds not observed.

OTHER CHARACTERISTICS

Disease and pest resistance: Neither resistance nor susceptibility to typical diseases and pests has been observed.

Drought tolerance: No tolerance for drought.

Temperature tolerance: USDA Zones 5-9.

What is claimed is:

1. A new and distinct cultivar of *Buxus* plant named 'BHGC01' as herein illustrated and described.

* * * * *